(12) United States Patent
Dukish

(10) Patent No.: US 9,978,271 B2
(45) Date of Patent: May 22, 2018

(54) INTERMITTENT ASYNCHRONOUS IR BEAM-BREAK FOG DETECTOR

(71) Applicant: Robert Allen Dukish, Canfield, OH (US)

(72) Inventor: Robert Allen Dukish, Canfield, OH (US)

( * ) Notice: Subject to any disclaimer, the term of this patent is extended or adjusted under 35 U.S.C. 154(b) by 0 days. days.

(21) Appl. No.: 15/484,758

(22) Filed: Apr. 11, 2017

(65) Prior Publication Data

US 2017/0345296 A1    Nov. 30, 2017

Related U.S. Application Data

(60) Provisional application No. 62/342,905, filed on May 28, 2016.

(51) Int. Cl.
| | |
|---|---|
| *H05B 37/02* | (2006.01) |
| *G01W 1/00* | (2006.01) |
| *G08G 1/09* | (2006.01) |
| *G01N 21/3504* | (2014.01) |

(52) U.S. Cl.
CPC ........... *G08G 1/09* (2013.01); *G01N 21/3504* (2013.01); *G01W 1/00* (2013.01); *H05B 37/0272* (2013.01); *H05B 37/0281* (2013.01)

(58) Field of Classification Search
CPC ........... H05B 37/0227; H05B 37/0218; H05B 37/0272; H05B 33/0824; H05B 33/0869; H05B 37/0245; H05B 37/0254; B64D 2203/00; B64F 1/205; E01F 9/559; E01F 9/662; F21S 8/022; F21S 9/02; F21V 5/02
See application file for complete search history.

(56) References Cited

U.S. PATENT DOCUMENTS

| | | | |
|---|---|---|---|
| 3,622,980 A * | 11/1971 | Elledge, Jr. | ...... G08G 1/096716 296/21 |
| 3,938,080 A | 2/1976 | Hulme | |
| 4,208,090 A | 6/1980 | Heenan | |
| 4,955,982 A | 9/1990 | Paulos | |
| 5,243,340 A | 9/1993 | Norman et al. | |
| 5,438,495 A | 8/1995 | Ahlen et al. | |
| 5,552,767 A | 9/1996 | Toman | |
| 5,839,816 A | 11/1998 | Varga et al. | |
| 5,984,570 A | 11/1999 | Parashar | |
| 6,092,909 A | 7/2000 | Sools et al. | |

(Continued)

OTHER PUBLICATIONS

U.S. Appl. No. 14/295,679, filed Jun. 4, 2014, Dukish.

*Primary Examiner* — Fekadeselassie Girma
(74) *Attorney, Agent, or Firm* — Robert J. Herberger; Robert G. Lev

(57) ABSTRACT

An automated roadway marker system that illuminates and provides warning and lane demarcation under poor visibility conditions utilizing IR beam-break transceivers where no deployment considerations need to be made for the first in a sequence, because each marker operationally establishes its linkage condition in an intermittently activated asynchronous pseudo-network. The devices are designed for extremely low power consumption, so that solar energy can be utilized as a power source. The markers can additionally be linked through radio frequency signals, and to provide a warning to mobile and stationary radio frequency receivers. Additionally, the markers can be illuminated via transmissions from mobile and stationary transmitters.

16 Claims, 5 Drawing Sheets

(56) References Cited

U.S. PATENT DOCUMENTS

| | | | |
|---|---|---|---|
| 6,354,714 B1 | 3/2002 | Rhodes | |
| 6,512,451 B1 | 1/2003 | Eslambolchl et al. | |
| 6,726,398 B2 | 4/2004 | Hamakawa et al. | |
| 7,109,850 B2 | 9/2006 | Kawazoe et al. | |
| 7,688,222 B2 | 3/2010 | Peddie et al. | |
| 8,427,076 B2 | 4/2013 | Bourquin et al. | |
| 9,142,130 B1 | 9/2015 | Dukish | |
| 2003/0053307 A1 | 3/2003 | Talamo et al. | |
| 2005/0030739 A1 | 2/2005 | Wang | |
| 2008/0243337 A1 | 10/2008 | Tsuda | |
| 2008/0286043 A1 | 11/2008 | Seo | |
| 2011/0062888 A1 | 3/2011 | Bondy et al. | |
| 2012/0074852 A1* | 3/2012 | Delnoij | H05B 37/0218 315/158 |
| 2013/0009553 A1* | 1/2013 | Lee | H05B 33/0824 315/153 |
| 2013/0113618 A1 | 5/2013 | Flanagan et al. | |
| 2015/0319825 A1* | 11/2015 | Destine | H05B 37/0227 315/153 |
| 2015/0353000 A1* | 12/2015 | Kowatzki | B60Q 1/24 315/77 |
| 2016/0198548 A1* | 7/2016 | Monaci | H05B 37/0218 315/152 |
| 2016/0338173 A1* | 11/2016 | Knaapen | H05B 33/0869 |
| 2017/0211247 A1* | 7/2017 | Messiou | E01F 9/559 |

* cited by examiner

US 9,978,271 B2

INTERMITTENT ASYNCHRONOUS IR BEAM-BREAK FOG DETECTOR

PRIORITY INFORMATION

The present application claims priority from U.S. Provisional Patent Application No. 62/342,905, filed on May 28, 2016.

TECHNICAL FIELD

The present invention relates generally to roadside, luminous marking devices activated when there is poor visibility along a roadway, for the purpose of alerting drivers and providing lane demarcation. In particular, the present invention is directed to an automatic roadside illumination system responsive to foggy road conditions.

BACKGROUND OF THE INVENTION

Many styles of present day markers aid in nighttime navigation for drivers along the roadways. Some are passive devices such as raised pavement markers and roadside reflectors. Active markers exist that illuminate in the presence of unsafe road conditions. Additionally, there are devices and methods for detecting the presence of foggy conditions, and providing aid in vehicle navigation by marking the roadway edges. Some systems provide a warning light to illuminate if an IR beam transmission between a transmitter and receiver is disrupted by the presence of fog. The conventional art for roadside illumination is well documented, with systems that cause an action to occur when a break in a beam is sensed. Such systems generally use an optical or IR transmitter on one end of the link, and an IR detector as a receiver on the other. Also included are "stand-alone" fog detection inventions that, rather than sensing a break in a beam, instead transmit a beam outward and sense a reflection off of the fog.

In U.S. Pat. No. 5,554,972, a perimeter warning system is presented in which an alarm is sounded if the continuity of a beam is broken. Additionally, warning systems have been developed to alert drivers to wildlife breaking the perimeter of a roadway, as shown in U.S. Pat. No. 8,410,941, where a break in a transmitted laser beam indicates that animals, such as deer, may be wandering into vehicular traffic areas.

Other systems use solar energy and marker devices in a network. In U.S. Pat. No. 9,142,130, a road safety device uses sound activation to illuminate a warning lamp. Additionally, solar energy is used to power a controller for detection of fog, and activate a plurality of wireless fog lamps, as disclosed in patent publication CN201412765.

In U.S. Pat. No. 7,235,786, a sensor for detecting fog-like media uses two emitted light beams and a receiver to determine the presence of fog through a process of reflection. Methods for utilizing optical or IR reflection of the marking device are also used to determine the presence of fog such as in patent CA1297085.

Until now, however, no easily deployable, low-power devices have been capable of providing a warning indication of pockets of poor visibility along a length of roadway that are self-contained transceivers.

SUMMARY OF THE INVENTION

The primary object of the present invention to provide a beacon system that conserves energy, while providing illumination for isolated pockets of fog.

Another object of the present invention is to provide a beacon system in which failure of one section of the system will not impact other sections of the system, thereby providing an effective fail-safe operation.

It is a further object of the present invention to provide a beacon system having independent beacons so that the system is self-healing when there are individual transmitter defects at individual beacons.

It is an additional object of the present invention to provide a beacon system that appears to be synchronized without the complexities and liabilities of actual synchronization.

It is still a further object of the present invention to provide a beacon system in which unintentional, or undesirable activation is avoided.

It is an additional object of the present invention to provide a beacon system that can be simply and easily deployed.

It is a further object of the present invention to provide a beacon system in which the necessity of lasers is avoided.

It is again another object of the present invention to provide a beacon system in which all of the units can be identical, thereby saving installation time and fabrication costs.

It is still a further object of the present invention to provide a beacon system that can be activated in a variety of different ways, responsive to poor visibility conditions, but also can be externally activated to aid in vehicular navigation.

These, and other goals and objects of the present invention, are achieved by a process of operating a beacon system, having multiple beacon units, in which the following steps are carried out. Responsive to at least one of a set of predetermined initiating conditions triggering at least partial activation of the beacon unit. Responsive to at least partial activation of a beacon unit, a link signal is sent to at least an adjacent beacon unit in the sequence of beacon units. Each beacon unit detects for a previously received link signal from an adjacent beacon unit, and full activation of the beacon unit is triggered responsive to detection of a previously sent link signal. Once absence of a link signal is detected in a fully activated beacon unit, a timing cycle is initiated responsive to the absence. During the long timing cycle, detection for receipt of a link signal is made. If the absence of the received link signal continues during a timing cycle, at least one beacon lamp is activated.

In another embodiment of the present invention, a beacon system having a plurality of beacon units is used. Each of the beacon units has at least one lamp and control apparatus. The plurality of beacons are arranged in a sequence along a travel route and configured so that each of the beacon units is at least partially activated by at least one of a set of predetermined initiating conditions. The sequence of beacons includes at least one initiating unit. The initiating unit is designated by non-receipt of a link signal, thereby resulting in not activation of a beacon lamp. The initiating unit includes an apparatus to send a link signal to a following beacon in the sequence. Also included is a plurality of identical following beacon units in the sequence, where each of the following beacon units is rendered fully operational by receipt of a link signal from a prior beacon unit in the sequence. The following beacon units operate so that a subsequent absence of a link signal over a predetermined timing cycle in any of the following beacon unit or units results in activation of at least one beacon lamp contained the following beacon unit or units.

DETAILED DESCRIPTION OF PREFERRED EMBODIMENTS

Figure 1:
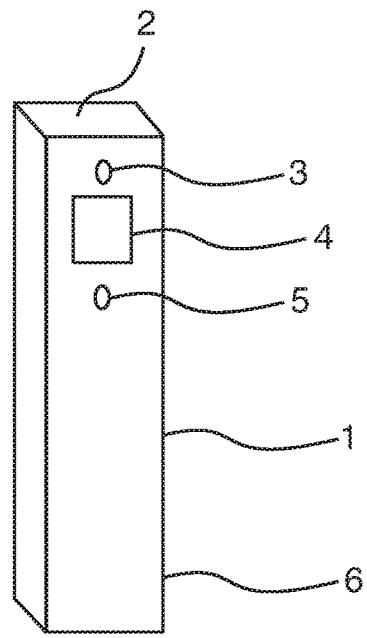
FIG. 1 is an illustration of the front view of a preferred housing.

The present invention solves the problem of difficult deployment of separate transmitters and receivers, while providing additional reliability in a perimeter beam-break system. Long distances can be covered without the use of lasers, by using a sequence of low power transceivers in a pseudo-network. Additionally, since each transceiver is designed to activate its marking light only after receiving a link signal from a previous transceiver, any defective markers are ignored and do not cause markers in the sequence to light unintentionally. In this way, the present invention provides a way to implement a system including a long path of road markers that appear to be networked, where each section of the chain is independent and self-healing, should an individual transceiver defect occur. Also, all devices in the system are identical, which allows for easy deployment, since there is no need to identify and place a specific transmitter device at the beginning of each chain of markers.

The present invention automatically disables the first beacon unit in a network to keep its receiver from erroneously responding to a non-linked condition, since it is the first in a sequence and therefore not positioned to receive any transmissions from previous devices. The upstream transceivers operate with self-contained approximate timers, so that no synchronization of signal transmission and reception is necessary. The system may also be considered self-healing, since there is no relaying of transmissions along the sequence of markers; a failure in a small section of the chain will not impact the entire network.

One preferred embodiment of the present invention consists of a solar powered marker stud which can be easily placed on the side of a roadway lane of travel. The device housing is similar in appearance to the flat plastic road studs that have reflectors attached to them, which are now in common use along roadways. One type of housing has an interior area in order to provide a hollow space used to accommodate electrical components.

In another embodiment, the main housing may be very similar to the aforementioned reflective road studs now in use, but with the majority of electrical components located at the stud's base, and inside of a watertight container. The housing of the inventive system may even have a visible reflector attached, and appear as a common road stud, but containing a lamp and a self-contained controller programmed to illuminate the marker lamp when poor visibility conditions occur. A housing designed for temporary use can also contain the device for use during emergency and special events. In yet another embodiment, the housing can be made such that it is easily affixed to existing roadway objects such as guard rails, bridge structures, fence posts, and other permanent objects.

The controller (20 in FIG. 7) is preferred to be a microprocessor, to allow for the best functionality, but the device could also be constructed from non-microprocessor based digital and analog devices such as RC networks, comparators, and IC timers such as the LM555. In the preferred embodiment, the transceiver function is controlled by a microprocessor program that uses an onboard "watchdog" timer to periodically transmit an infrared carrier signal of a specific pulse time duration as a coded signal. The very first transmission of said signal, establishes a link, and subsequent transmissions verify that the link is intact. A break in the established link would occur if the visibility between transceivers became poor, and unable to pass the IR link signal through the air. This condition could be caused by a variety of environmental factors including: fog, rain, dust, and snow, and would illuminate a marker lamp. Once the visibility improved, the microprocessor program establishes a reset condition to extinguish the marker lamps.

The transmitters and receivers contained in each marker are not synchronized with other markers in the network, but each has an onboard "watchdog" timer set to the approximate time that a link pulse should occur. If a previous marker sends the initial link signal to activate the link between markers, then subsequent transmitted signals cause the receiving controller not to illuminate the marker lamp. Because there is no direct synchronization, if no link signal is received, the receiving controller waits for a few watchdog time intervals before lighting the lamp of the marker to which it is attached, so as to not falsely react due to time skew. Using its timer, the controller also periodically transmits a link signal upstream to the next in a series of markers.

The system appears to be networked in operation. However, by not needing to periodically transmit direct synchronization information, or act as a relay, electrical power is conserved. Since poor roadway visibility generally occurs slowly over time, additional power is conserved with the onboard timers used to transmit and check for the reception of link signals, having a somewhat long pause duration when compared to the link pulsewidth (i.e., the onboard timer may have a repetition rate of minutes, whereas the pulsewidth of the transmitted signal may be in the millisecond range.)

In the preferred embodiment using a microprocessor as a controller, inbetween timer activity, the controller can be put into sleep mode to further conserve power. If a link signal is received from the previous marker, it can cause an interrupt to occur to wake the controller.

During daylight the markers are charged by solar energy and remain inoperative until nightfall. Even during a nighttime low-visibility event, power can additionally be conserved by having the marker lamp be responsive to the sound of nearby vehicular traffic so that it is extinguished if no one is using the roadway near the marker. Maximum power conservation is an important feature of the present invention. The beacons must reliably activate the beacon lamps due to the safety hazard of vehicles accidentally impacting unlit beacons. This safety concern necessitates that the marking device make the smallest footprint as possible (i.e., using small storage batteries, small solar collecting cells, and other components). Energy efficiency is also an important factor since the device must remain operational throughout an entire night and during occasional adverse weather conditions during the day.

Figure 2:
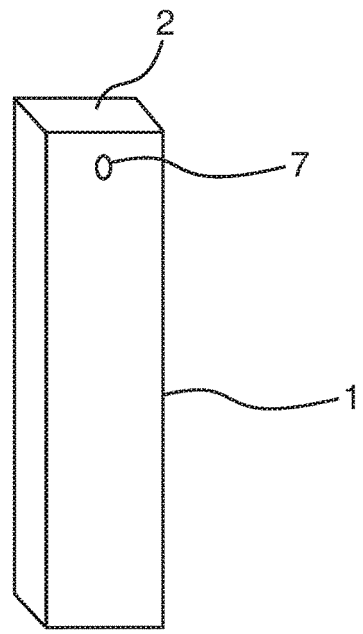
FIG. 2 is an illustration of the back view of the preferred housing of FIG. 1.

Referring to FIG. 1, the housing of the invention can consist of an elongated rectangular prism shape 1, with a hollow interior for electrical components. On the top face 2, a solar energy collection plate can be affixed horizontally, or can be mounted to the surface at an angle. The solar energy storage cells would be located near the base 6. The front face would be deployed toward oncoming vehicular traffic and contain a marker lamp 4, which provides a visual indication to nearby drivers of lane demarcation during low visibility conditions. Microphone 5 can be used to respond to vehicular acoustical vibrations in order to assist in identifying nearby vehicular activity. The low visibility condition is sensed when IR receiver 3, detects a beam-break in the link signal transmitted from the back face of the previous marker. The link signal is transmitted by the emitter 7 in FIG. 2, which consists of one or more IR LED emitters.

Figure 3:
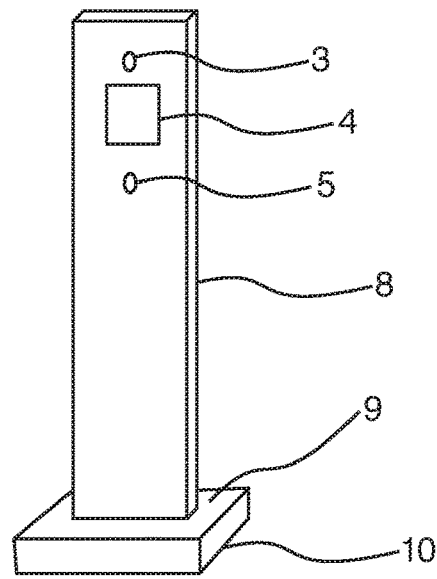
FIG. 3 is an illustration of the front view of an alternative housing.
Figure 4:
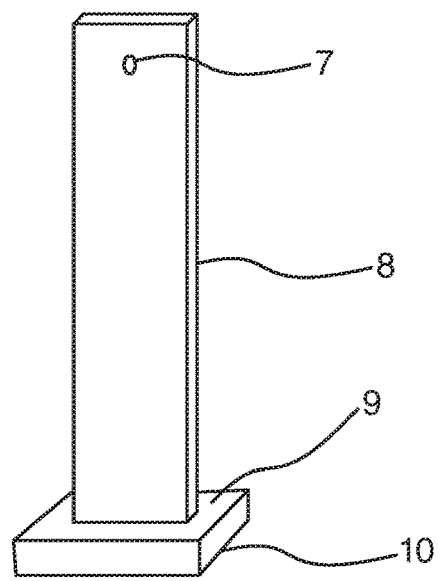
FIG. 4 is an illustration of the back view of the alternative housing of FIG. 3.

In FIG. 3, for reasons of additional safety, one of the alternate housings 8, is shown in which the solar energy collector plate is affixed or attached to the surface of face 9, positioned lower and closer to the ground and near the base of the housing where a watertight base 10 contains solar energy storage cells. FIG. 4 is very similar to FIG. 2, with the exception of the changes outlined in FIG. 3 which also provides for an overall thinner elongated rectangular prism marker shape.

Figure 5:
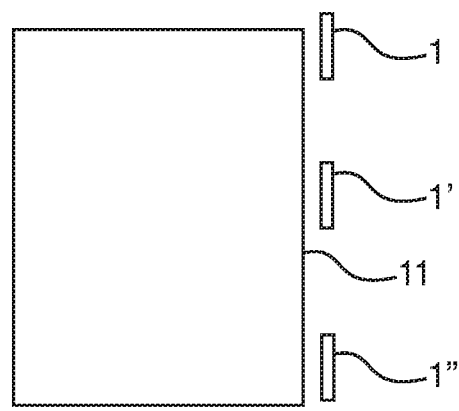
FIG. 5 is a representative depiction of the positioning of the markers along a segment of roadway.

The physical placement along a roadway is shown in FIG. 5 where at the edge of the lane 11 of a road section, markers 1, 1', 1", etc., are positioned so that their marker lamps 4, as shown in FIG. 1 and FIG. 3, are visible to drivers traveling the roadway.

Figure 6:
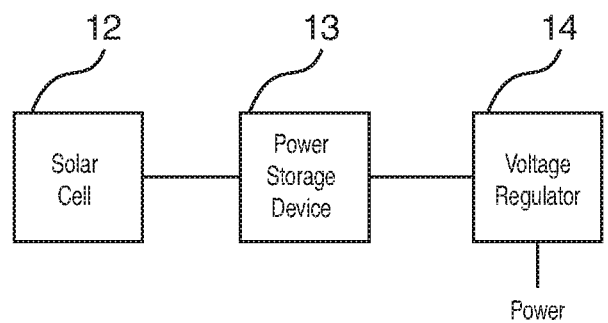
FIG. 6 is a block diagram of the power unit.

In FIG. 6, the power supply is schematically depicted. Solar cell plate 12, would be positioned on either top surface face 2 or surface 9 as shown in FIGS. 1-2, and 3-4, respectively. Solar energy storage cells 13 would be positioned near the bottom of FIGS. 1-2 or in the base 10 of FIGS. 3-4. The voltage regulator 14 would be contained within the housings and able to supply a continuous DC voltage needed to operate the sensing, control, and warning circuits as shown in the following Figures.

Figure 7:
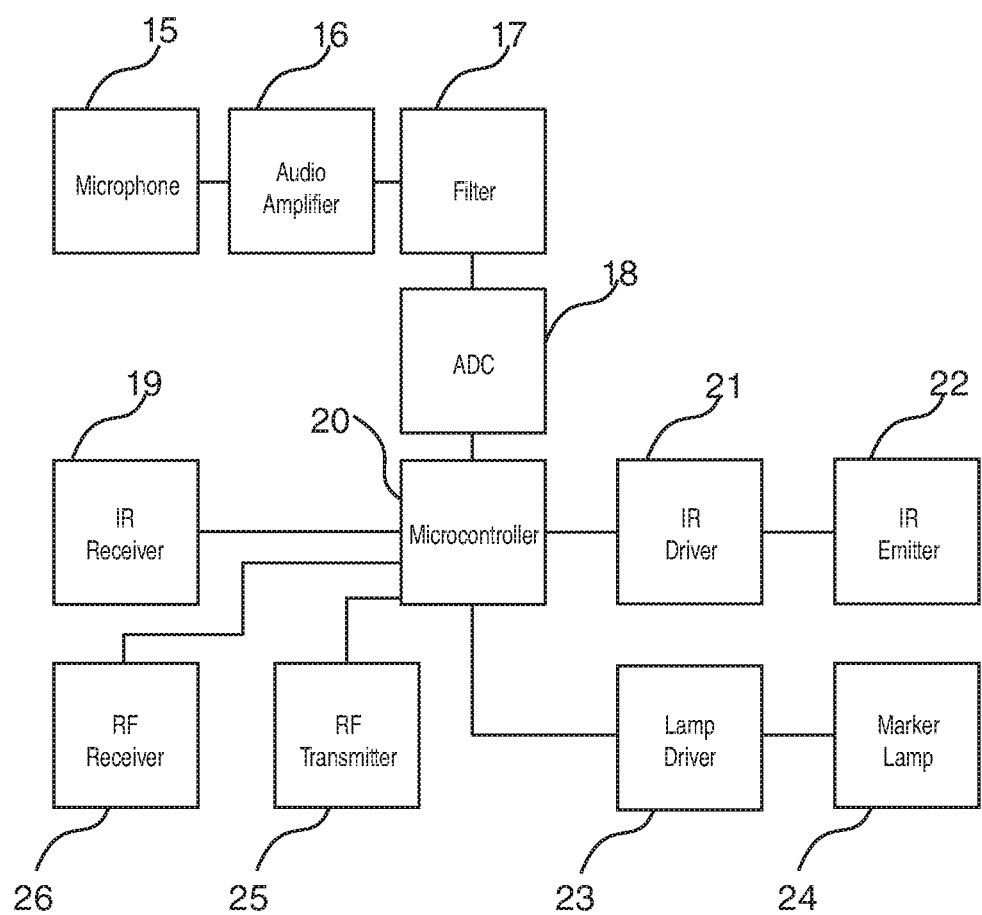
FIG. 7 is a block diagram of the transceiver with a microprocessor controller in one embodiment of the present invention.

Referring to the functional block diagram of FIG. 7, once IR receiver 19 detects an incoming signal of the proper carrier frequency, it produces an output which is read by microcontroller 20. If the program of microcontroller 20 determines the incoming signal is a valid link signal (due to a previously sensed signal which causes the activation mode of microcontroller 20 to engage), then no action is taken to initiate a warning condition. If, however, a warning condition is initiated because of an absence of valid link signals after a number of onboard watchdog timer cycles have passed, then the program can activate lamp driver 23 to illuminate the marker's warning lamp 24. In the alternative the microcontroller can be programmed to seek additional warning lamp triggering information received by microphone 15, amplified by audio amplifier 16, and selected by filter 17, and then digitized by analog to digital converter 18 (i.e., ADC). If the resulting audio data is of the correct amplitude intensity and frequency to signify nearby traffic, microcontroller 20 could then light the marker warning lamp. RF receiver 26 is an auxiliary input to microprocessor 20 and can signal an activation event, irrespective of a signal from IR receiver 19. If the program of microcontroller 20 determines that the individual marker warning needs to be initiated, the proper logic level is than output to enable lamp driver 23, which then causes marker lamp 24 to illuminate.

Also microcontroller 20 could than enable RF transmitter 25 to broadcast that an activation of the marker 1 or 8, shown respectively in FIGS. 1 and 3, has occurred. Regardless of the activation of the marker lamp 24, the microcontroller 20 periodically sends a logic level to IR driver 21 in order to send the proper IR link pulses upstream from IR emitter 22, to additional markers shown in FIG. 5 as markers 1, 1', 1", and so forth.

Other embodiments using the device explained above can further contain communication modules such as: 1) a radio frequency (RF) transmitter capable of signal transmissions to nearby vehicles equipped with a corresponding receiver; 2) an RF transmitter capable of sending data to an internet link, whereby the fog warning indication can be accessed by mobile devices such as smartphones and vehicle navigation units; 3) an RF receiver module interfaced to the marker controller so that transmission from a base station can activate marker lamps 24 in cases of emergency and special events; and/or 4) an RF receiver interfaced to the marker controller so that a transmission from a mobile station such as a smartphone or vehicle navigation system can activate the marker lamp. The operation of this system is explained with the use of a microcontroller programming logic flow-chart, as depicted in FIG. 8.

Figure 8:
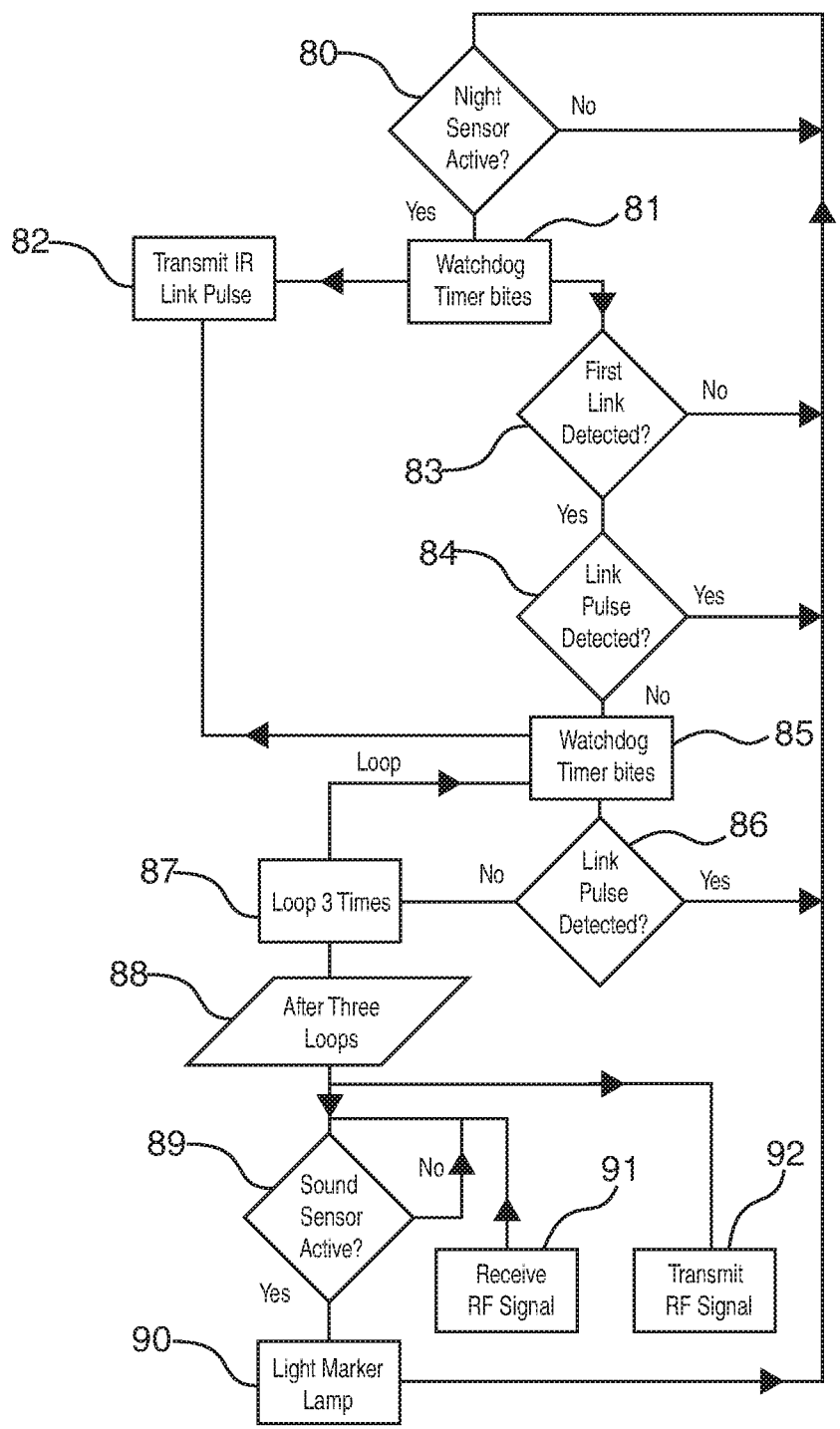
FIG. 8 is a flow diagram depicting another operation of the present invention.

In the first step of FIG. 8, if the solar cell 12 (depicted in FIG. 6) is not developing enough energy to charge power storage device 13, the unit is in darkness (step 80). This condition triggers watchdog timer (steps 81 and 85), and the operational program is activated. At every preset interval of the watchdog timers, a transmit link is sent (step 82) through microcontroller 20, IR driver 21, and IR emitter 22 (depicted in FIG. 7).

Additionally, the watchdog timer operation (steps 81 and 85) is the impetus that queries the program to check for IR signal linkage from a previous marker (step 83) to identify that the current marker is not the first in a series of markers (step 84). If no previous markers are linked, then the program will not light the marker lamp (step 90), indicating a link loss condition. This operating arrangement keeps the first in a series of makers from erroneously lighting.

However, if a link signal from a previous marker has been received (step 83), then subsequent receptions of the link signal (step 84) will keep the marker lamp extinguished. Since the sequence of markers in the pseudo-network are asynchronous, timing skew can develop, so the microcontroller program will wait for a number of time intervals to pass (step 87) before determining that an IR link (steps 86 and 88) has truly become inactive.

If the marker had been successfully linked (step 83), and the link pulses from a previous marker's IR emitter become inactive (steps 86, 87, 88), then the program will determine that a warning condition is warranted. The program will illuminate the marker warning light (step 90). The program may also transmit an RF signal (step 92) to a mobile or stationary receiver.

For energy efficiency, sound may be detected (step 89) to assure that a vehicle is proximate to the marker before the lamp illumination will occur. As the program loops, if an inactive IR link is reestablished, then the warning condition is reset (step 83).

Additionally, with the use of an onboard RF receiver (step 91), local link conditions can be overridden at any time, so that the marker lamp is under the direct control of an external transmitter which can use the maker's illumination for use as a navigation aid, or to illuminate the marker for special conditions and events from either a mobile or stationary transmitter.

It will be seen that a unique and novel roadside, luminous marking device system, utilizing intermittent, asynchronous IR beam-break detection for the purpose of alerting drivers to low-visibility conditions, has been illustrated and described. It will be apparent to those skilled in the art that various changes and modifications may be made therein without departing from the spirit of the invention. Accordingly, the present invention should be interpreted to include any and all variations, modifications, derivations, adaptations, and embodiments that would occur to one skilled in this art, having possession of the teachings of the present application. Therefore, the present invention should be construed as being limited only by the following claims.

The invention claimed is:

1. A process for operating a beacon system responsive to at least one of a plurality of predetermined initiating conditions, said beacon system having multiple beacon units, with each unit having at least one lamp, said beacon units being arranged in a sequence along a travel route, each of said beacon units having transmission capability to link to at least one adjacent beacon unit in said sequence, and being responsive to a link signal from a second adjacent beacon unit, said process comprising:
   a) transmitting link signals from said beacon units to trigger at least partial activation of the corresponding one adjacent beacon unit;
   b) automatically detecting a received link signal from the corresponding second adjacent unit in said sequence and triggering partial activation of a receiving beacon unit upon detection of said received link signal;
   c) in the partially activated beacon unit detecting for a continuing absence of said received link signal, and initiating a predetermined timing cycle responsive to said continuing absence of said link signal;
   d) detecting for receipt of a reestablishing link signal in the partially activated beacon unit during said predetermined timing cycle;
   e) fully activating said partially activated beacon unit responsive to the absence of the reestablishing link signal for the duration of said predetermined timing cycle;
   f) detecting vehicular traffic near said fully activated beacon unit; and,
   g) illuminating said at least one lamp associated with said fully activated beacon responsive to detection of vehicular traffic, wherein absence of said reestablished link signal is indicative of said at least one of the plurality of predetermined initiating conditions selected from a group including fog, snow, rain and dust.

2. The process of claim 1, wherein each said beacon unit transmits said link signal in a single direction to the corresponding adjacent beacon unit.

3. The process of claim 2, wherein one of said beacon units in said sequence is partially activated when at least one of said set of said predetermined initiating conditions is detected.

4. The process of claim 3, wherein the step of transmitting said link signal from a beacon unit to a corresponding adjacent beacon unit is delayed by the predetermined time cycle.

5. The process of claim 4, wherein said predetermined timing cycle is longer than a cycle of said link signal.

6. The process of claim 5, wherein said link signal comprises an infrared pulse sequence.

7. The process of claim 1, wherein full activation of said beacon lamps can be triggered by receipt of an external radio signal.

8. The process of claim 7, wherein said external radio signal is of a predetermined characteristic necessary to activate said beacon lamps.

9. The process of claim 8, wherein an internet connection is utilized to provide link signals.

10. The process of claim 1, wherein at least one beacon unit transmits an external radio signal.

11. A beacon system responsive to at least one of a plurality of predetermined initiating conditions, said beacon system having multiple beacon units arranged in a sequence along a travel route, each unit having a controller with a transmitter to send a link signal to a first adjacent beacon unit and receiver to detect a link signal transmitted from a second adjacent beacon unit in said sequence, said system comprising:
   a) an initiating beacon unit among the multiple beacon units, said initiating beacon unit having a timer for measuring a length of interruption of the link signal from the corresponding second adjacent beacon unit for comparison to a predetermined timing cycle;
   b) a traffic noise detector in communication with said initiating beacon unit; and,
   c) at least one lamp for illumination in communication with said initiating beacon unit responsive to detection of vehicular traffic by the traffic noise detector, wherein continued absence of the link signal from the corresponding second adjacent beacon unit for a time longer than the predetermined timing cycle is indicative of said at least one of the plurality of predetermined initiating conditions selected from a group including fog, snow, rain and dust.

12. The beacon system of claim 11, further comprising at least one independent timing device and beacon lamp in each said beacon unit.

13. The beacon system of claim 11, wherein said link signal comprises a sequence of infrared pulses.

14. The beacon system of claim 13, further comprising an infrared transmitter in each said beacon unit, each said infrared transmitter being configured to transmit said link signal as an infrared pulse in a single direction.

15. The beacon system of claim 11, further comprising a means for receiving external radio frequency signals to remotely activate at least one of said multiple beacon units.

16. The beacon system of claim 11, further comprising a means to transmit external radio frequency alarm signals for reception by a mobile or land based receiver unit.

* * * * *